(12) United States Patent
Poh

(10) Patent No.: US 9,913,588 B2
(45) Date of Patent: Mar. 13, 2018

(54) METHOD AND SYSTEM FOR SCREENING OF ATRIAL FIBRILLATION

(71) Applicant: Cardiio, Inc., Cambridge, MA (US)

(72) Inventor: Ming-Zher Poh, Cambridge, MA (US)

(73) Assignee: Cardiio, Inc., Cambridge, MA (US)

( * ) Notice: Subject to any disclaimer, the term of this patent is extended or adjusted under 35 U.S.C. 154(b) by 0 days.

(21) Appl. No.: 14/833,010

(22) Filed: Aug. 21, 2015

(65) Prior Publication Data

US 2015/0359443 A1    Dec. 17, 2015

Related U.S. Application Data

(63) Continuation of application No. 14/528,050, filed on Oct. 30, 2014.
(Continued)

(51) Int. Cl.
*A61B 5/0295* (2006.01)
*A61B 5/024* (2006.01)
(Continued)

(52) U.S. Cl.
CPC .......... *A61B 5/0295* (2013.01); *A61B 5/0261* (2013.01); *A61B 5/02405* (2013.01);
(Continued)

(58) Field of Classification Search
CPC . A61B 5/02405; A61B 5/7275; A61B 5/7264; A61B 5/7246; A61B 5/0295;
(Continued)

(56) References Cited

U.S. PATENT DOCUMENTS 5,846,189 A * 12/1998 Pincus ................. A61B 5/0452
128/897
5,853,364 A * 12/1998 Baker, Jr. ........... A61B 5/02416
367/155
(Continued)

FOREIGN PATENT DOCUMENTS

WO    2005067790 A1    7/2005
WO    2010073908 A1    7/2010
(Continued)

OTHER PUBLICATIONS

Verkruysee et al., Remote plethysmographic imaging using ambient light, Opt Express. Dec. 22, 2008; 16(26): 21434-21445.*
(Continued)

*Primary Examiner* — Bo J Peng
(74) *Attorney, Agent, or Firm* — Loginov & Associates; William A. Loginov

(57) ABSTRACT

The present disclosure provides a description of various methods and systems associated with determining possible presence of Atrial Fibrillation (AF). In one example, a camera of a client device, such as a mobile phone, may acquire a series of images of a body part of a user. A plethysmographic waveform may be generated from the series of images. An autocorrelation function may be calculated from the waveform, and a number of features may be computed from the autocorrelation function. Based on an analysis of the features, a determination may be made about whether the user is experiencing AF. Such determined may be output to a display of the mobile phone for user review.

17 Claims, 8 Drawing Sheets

Related U.S. Application Data

(60) Provisional application No. 61/899,098, filed on Nov. 1, 2013.

(51) Int. Cl.
  *A61B 5/026* (2006.01)
  *A61B 5/00* (2006.01)

(52) U.S. Cl.
  CPC ........ *A61B 5/02416* (2013.01); *A61B 5/6898* (2013.01); *A61B 5/7246* (2013.01); *A61B 5/7264* (2013.01); *A61B 5/7275* (2013.01); *A61B 5/7282* (2013.01); *A61B 5/02438* (2013.01); *A61B 2576/023* (2013.01)

(58) Field of Classification Search
  CPC . A61B 5/0261; A61B 5/02416; A61B 5/6898; A61B 5/7282; A61B 2576/023
  See application file for complete search history.

(56) References Cited

U.S. PATENT DOCUMENTS

| | | | |
|---|---|---|---|
| 7,020,514 B1 * | 3/2006 | Wiesel | A61B 5/046 600/508 |
| 7,190,994 B2 | 3/2007 | Molhler et al. | |
| 7,283,870 B2 | 10/2007 | Kaiser et al. | |
| 7,593,772 B2 | 9/2009 | Sherman | |
| 7,846,106 B2 | 12/2010 | Andrews et al. | |
| 2003/0212336 A1 * | 11/2003 | Lee | A61B 5/02416 600/504 |
| 2005/0070808 A1 | 3/2005 | Marks et al. | |
| 2007/0213624 A1 * | 9/2007 | Reisfeld | A61B 5/0402 600/504 |
| 2007/0276270 A1 * | 11/2007 | Tran | A61B 5/0022 600/508 |
| 2008/0214903 A1 | 9/2008 | Orbach | |
| 2011/0196244 A1 * | 8/2011 | Ribas Ripoll | A61B 5/021 600/485 |
| 2011/0251493 A1 | 10/2011 | Poh et al. | |
| 2013/0006126 A1 | 1/2013 | Band et al. | |
| 2013/0041273 A1 | 2/2013 | Houben et al. | |
| 2013/0184573 A1 | 7/2013 | Pahlevan et al. | |
| 2013/0324812 A1 * | 12/2013 | Brainard, II | A61B 5/0205 600/324 |
| 2014/0073975 A1 * | 3/2014 | Engelbrecht | A61B 5/7203 600/502 |
| 2014/0205165 A1 * | 7/2014 | Jeanne | A61B 5/117 382/128 |

FOREIGN PATENT DOCUMENTS

| | | |
|---|---|---|
| WO | 2013020710 A1 | 2/2013 |
| WO | 2013027141 A2 | 2/2013 |

OTHER PUBLICATIONS

Bootsma, "Analysis of R-R Intervals in Patients With Atrial Fibrillation at Rest and During Exercise", "Circulation", May 1, 1970, pp. 783-794, vol. XLI, Publisher: Department of Cardiology, University Hospital, Published in: NL.

Chen, et al., "Ventricular Fibrillation Detection by a Regression Test on the Autocorrelation Function", "Medical & Biological Engineering & Computing", May 1, 1987, pp. 241-249, vol. 25, Publisher: IFMBE, Published in: US.

Poh, et al., "Advancements in Noncontact, Multiparameter Physiological Measuring Using a Webcam", "IEEE Transactions on Biomedical Engineering", Oct. 14, 2010, pp. 7-11, vol. 58, No. 1, Publisher: IEEE, Published in: US.

Jinseok, et al., "Atrial Fibrillation Detection Using an iPhone 4S", "IEEE Transactions on Biomedical Engineering", Jul. 31, 2013, pp. 203-206, vol. 60, No. 1, Publisher: IEEE, Published in: US.

Scully, et al., "Physiological Parameter Monitoring From Optical Recordings With a Mobile Phone", "IEEE Transactions on Biomedical Engineering", Jul. 29, 2011, pp. 303-306, vol. 59, No. 2, Publisher: IEEE, Published in: US.

Bravi, et al., "Review and Classification of Variability Analysis Techniques With Clinical Applications", Oct. 10, 2011, pp. 127, vol. 10, No. 1, Publisher: BioMedical Engineering Online, Published in: US.

Thakker, et al., "Wrist Pulse Signal Classification for Health Diagnosis", "4th International Conference on Biomedical Engineering and Informatics", Oct. 15, 2011, pp. 1799-1805, Publisher: IEEE, Published in: US.

* cited by examiner

METHOD AND SYSTEM FOR SCREENING OF ATRIAL FIBRILLATION

RELATED APPLICATIONS

This application is a continuation of co-pending U.S. patent application Ser. No. 14/528,050, filed Oct. 30, 2014, entitled METHOD AND SYSTEM FOR SCREENING OF ATRIAL FIBRILLATION, which application claims the benefit of U.S. Provisional Application Ser. No. 61,899,098, filed Nov. 1, 2013, entitled METHOD AND SYSTEM FOR SCREENING OF ATRIAL FIBRILLATION, the entire disclosures of each of which applications are herein incorporated by reference.

FIELD OF THE INVENTION

This invention relates to the field of patient monitoring to detect atrial fibrillation.

BACKGROUND OF THE INVENTION

The heart functions to pump blood to the rest of the body. It contains two upper chambers called atria and two lower chambers called ventricles. During each heartbeat, the atria will first contract, followed by the ventricles. The timing of these contractions is important to allow for efficient circulation. This is controlled by the heart's electrical system.

The sinoatrial (SA) node acts as the heart's internal pacemaker and signals the start of each heartbeat. When the SA node fires an impulse, electrical activity spreads through the left and right atria, causing them to contract and squeeze blood into the ventricles. The impulse travels to the atrioventricular (AV) node, which is the only electrical bridge that connects the atrial and ventricular chambers. The electrical impulse propagates through the walls of the ventricles, causing them to contract and pump blood out of the heart. When the SA node is directing the electrical activity of the heart, the rhythm is referred to as normal sinus rhythm (NSR).

Atrial fibrillation (AF) is the most common sustained heart rhythm disorder. Instead of the SA node directing electrical rhythm, many different impulses rapidly fire at once, producing a rapid and highly irregular pattern of impulses reaching the AV node. The AV node acts as a filter to limit the number of impulses that travel to the ventricles, but many impulses still get through in a fast and disorganized manner. As such, the hallmark of AF is an irregular rhythm where the ventricles beat in a very chaotic fashion.

AF presents a major risk factor for stroke. Due to the fast and chaotic nature of electrical activity, the atria cannot squeeze blood effectively into the ventricles. This results in abnormal blood flow and vessel wall damage that increases the likelihood of forming blood clots. If a clot is pumped out of the heart, it can travel to the brain and cause a stroke. People with AF are 5 times more likely to experience a stroke compared to the general population. Three out of four AF-related strokes can be prevented if a diagnosis is available, but many people who have AF don't know it because they may not feel symptoms.

The gold standard for diagnosing AF is the visual inspection of the electrocardiogram (ECG). This relies on AF being present at the time of an in-clinic ECG recording but AF may occur only intermittently. Furthermore, AF would remain undetected in patients who are asymptomatic. As such, there is a need for a more effective screening strategy that can be easily deployed to the general population. The increasing availability of smart phone technology for measuring the blood volume pulse, or plethysmographic waveform presents a growing opportunity for automated detection of AF.

Prior algorithms on automatic AF detection are based primarily on R-R interval variability or rely on the absence of P-waves in the ECG. However, applying these ECG-based techniques to the plethysmographic waveform is non-trivial because the plethysmographic waveform is very different from the ECG. The plethysmogram reflects changes in blood volume as the arterial pulse expands and contracts the microvasculature whereas the ECG reflects electrical activity of the heart. P-waves are not available for analysis in the plethysmogram. Unlike the ECG, the plethysmogram lacks a signature peak such as the QRS complex. This lack of an easily distinguishable peak, coupled with sensor movement, severity of motion artifacts, and the presence of dicrotic notches, pose a significant problem in the accuracy of beat-to-beat interval measurements derived from the plethysmographic waveform. This is particularly problematic when plethysmographic waveforms are acquired remotely in a contact-free manner.

It is therefore desirable to provide a method that can robustly differentiate AF from NSR and other common heart rhythm abnormalities using plethysmographic waveforms. It is further desirable that the method be able to work even with recordings of short duration (under 1 minute).

It is also desirable to have a simple system capable of detecting the possible presence of AF and communicating this condition to the user such that the user is alerted to consult a medical practitioner for further testing and/or treatment.

SUMMARY OF THE INVENTION

An illustrative embodiment of the disclosure provides a method for detecting presence of atrial fibrillation, the method including: acquiring a plethysmographic waveform; calculating an autocorrelation function of the plethysmographic waveform; computing at least one feature from the autocorrelation function; and analyzing, using a processor, the at least one feature from the autocorrelation function to determine presence of atrial fibrillation.

In one example, acquiring the plethysmographic waveform includes acquiring the plethysmographic waveform using a sensor.

In one example, the sensor includes a camera.

In one example, the camera includes a camera with self-contained optics.

In one example, acquiring the plethysmographic waveform includes: a) capturing a series of images from a body part; b) identifying a region of interest; c) separating the series of images into one or more channels; and d) averaging pixels within the region of interest.

In one example, the sensor includes at least one light sensor configured to receive light from a light source.

In one example, computing the at least one feature includes computing at least one feature from the group including: area-under-curve; a variation between autocorrelation coefficients; a complexity of the autocorrelation function; an amplitude of the first non-zero-lag peak in the autocorrelation function.

In one example, the at least one feature includes: extracting a sequence of peak-amplitudes from the autocorrelation function using a peak detection algorithm.

In one example, the at least one feature further includes at least one from the group including: computing time intervals between the peak-amplitudes of the autocorrelation function; computing variation between peak-amplitudes of the autocorrelation function; computing complexity between peak-amplitudes of the autocorrelation function; computing variation of time-intervals between peaks of the autocorrelation function; and computing complexity of peak-to-peak time-intervals of the autocorrelation function.

In one example, the at least one feature further comprises computing a strength of a monotone association between peak-amplitudes and corresponding lag times.

In one example, the at least one feature comprises comparing a value determined from the feature to a threshold value for the feature.

In one example, analyzing the at least one feature comprises analyzing a plurality of features, each of the features being compared to respective threshold values.

In one example, analyzing the at least one feature comprises analyzing a plurality of features using a classification function.

In one example, the method further includes displaying a result of the AF determination.

In one example, the method further includes displaying an AF probability.

Another aspect of the disclosure provides a system for detecting presence of atrial fibrillation, the system including: a sensor for acquiring a plethysmographic waveform; a processor configured for calculating an autocorrelation function of the plethysmographic waveform, computing at least one feature from the autocorrelation function, and analyzing the at least one feature to determine presence of atrial fibrillation.

Another aspect of the disclosure provides a method of detecting presence of atrial fibrillation at a client device, the method including: capturing a series of images of at least a portion of a user; generating a plethysmographic waveform from the series of images; calculating an autocorrelation function of the plethysmographic waveform; computing at least one feature from the autocorrelation function; analyzing, using a processor, the at least one feature from the autocorrelation function to determine presence of atrial fibrillation.

Another aspect of the disclosure provides a method for monitoring the status of atrial fibrillation of an individual and providing feedback to a user, the method including: acquiring a plethysmographic waveform; calculating an autocorrelation function of the plethysmographic waveform; computing at least one feature from the autocorrelation function; analyzing, using a processor, the at least one feature from the autocorrelation function; and providing at least one recommended course of action based upon the analysis of the at least one feature from the autocorrelation function.

In one example, the at least one recommended course of action includes at least one action from the group including: scheduling an appointment with a care provider, consulting a care provider, adjusting medication levels, modifying diet, and modifying exercise patterns.

BRIEF DESCRIPTION OF THE DRAWINGS

The description below refers to the accompanying drawings, of which:

FIGS. 3A and 3B show a plethysmogram and its autocorrelation function in NSR, respectively. FIGS. 3C and 3D show a plethysmogram and its autocorrelation function in AF, respectively;

FIGS. 6A and 6B respectively show the detected peaks of an autocorrelation function in NSR and the resulting sequence of time intervals between peaks. FIGS. 6C and 6D respectively show the detected peaks of an autocorrelation function in AF and the resulting sequence of time intervals between peaks;

DETAILED DESCRIPTION

The present disclosure provides a description of various methods and systems associated with determining possible presence of Atrial Fibrillation (AF). In an illustrative embodiment, a camera of a client device, such as a mobile phone, may acquire a series of images of a body part of a user. A plethysmographic waveform may be generated from the series of images. An autocorrelation function may be calculated from the waveform, and a number of features may be computed from the autocorrelation function. Based on an analysis of the features, a determination may be made about whether the user is experiencing AF. Such determination may be output to a display of the mobile phone for user review.

Figure 1:
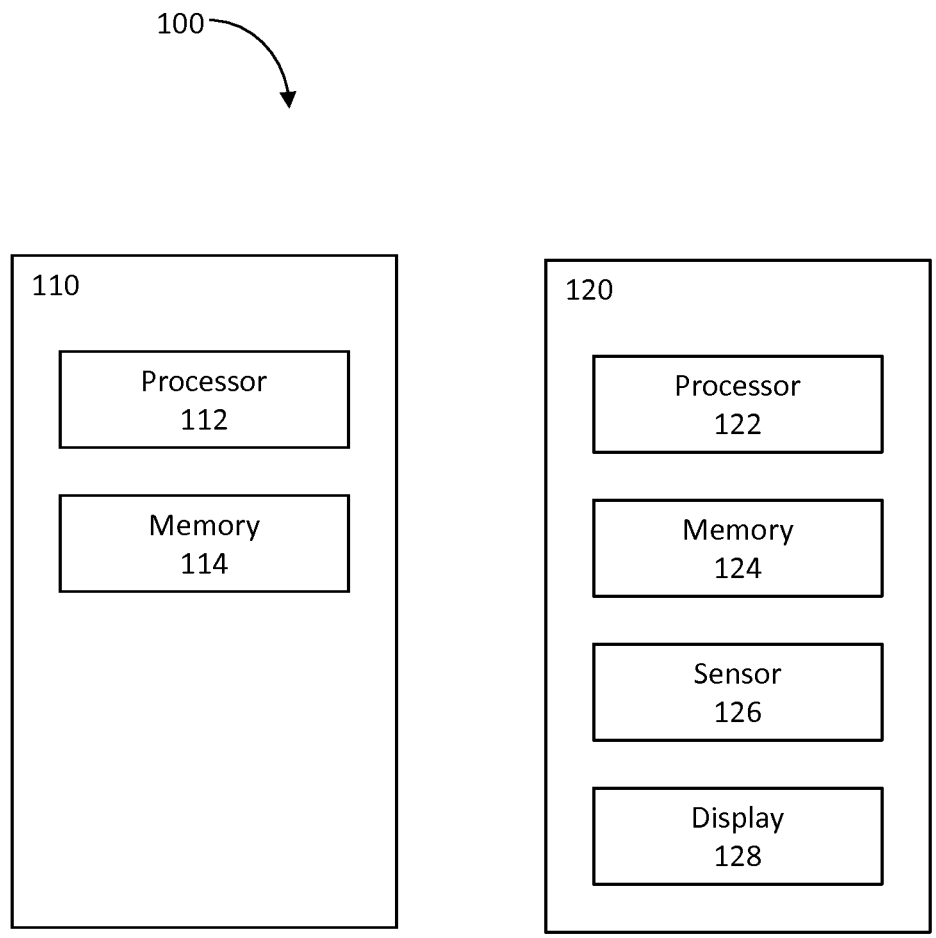
FIG. 1 is a block diagram of a system for detecting AF according to aspects of the disclosure.

FIG. 1 is a block diagram of a system 100 for detecting presence of AF according to aspects of the disclosure. As shown, the system 100 may include a computer 110 and a client device 120.

The computer 110 may include a processor 112, a memory 114, and any other components typically present in general purpose computers. The memory 114 may store information accessible by the processor 112, such as instructions that may be executed by the processor or data that may be retrieved, manipulated, or stored by the processor. Although FIG. 1 illustrates processor 112 and memory 114 as being within the same block, it is understood that the processor 112 and memory 114 may respectively comprise one or more processors and/or memories that may or may not be stored in the same physical housing. In one example, computer 110 may be a server that communicates with one or more client devices 120, directly or indirectly, via a network (not shown).

The client device 120 may be configured similarly to the computer 110, such that it may include processor 122, a memory 124, and any other components typically present in a general purpose computer. The client device 120 may be any type of computing device, such as a personal computer, tablet, mobile phone, laptop, PDA, etc.

The client device 120 may also include a sensor 126. The sensor 126 may be an imaging device, such as an image sensor, e.g., camera. The camera may be any type of camera, such as a digital camera including self-contained optics. In other examples, the camera may have several components, such as lenses, other optics, and processing circuitry that may or may not be housed within a single housing. The client device 120 may also include a display 128, such as an LCD, plasma, touch screen, or the like.

Figure 2:
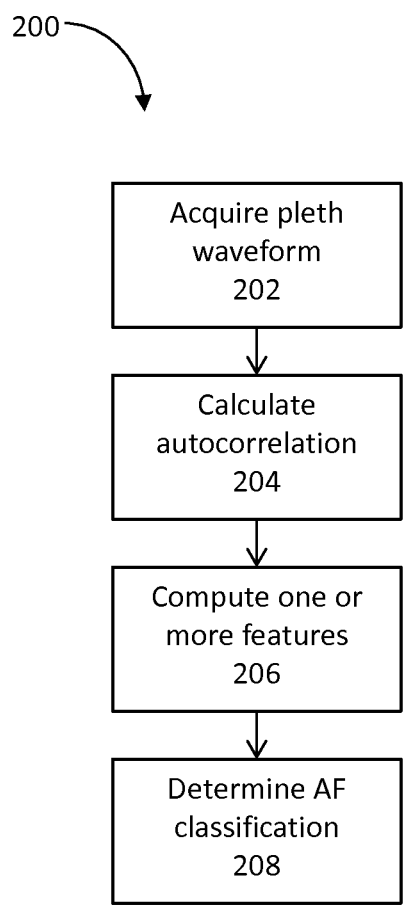
FIG. 2 is a flowchart illustrating an overview of a method for detecting AF according to aspects of the disclosure.

FIG. 2 is a flowchart illustrating an overview of a method 200 for detecting AF according to aspects of the disclosure. At block 202, a plethysmographic waveform is acquired. At block 204, autocorrelation is performed on the plethysmographic waveform, yielding an autocorrelation function of the plethysmographic waveform. At block 206, one or more features may be computed from the autocorrelation function of the plethysmographic waveform. At block 208, an AF determination may be made based on the one or more features computed from the autocorrelation function. It should be appreciated that one or more of the blocks 202-208, or any subprocesses or subroutines associated therewith may be performed at either or both of the computer 110 or the client device 120. In some examples, some of the blocks may be performed at the computer 110, while other of the blocks may be performed at the client device 120. Each of the blocks will now be described in greater detail below.

Acquiring Plethysmographic Waveform

At block 202, the sensor 126, such as a camera, may be used to capture video input of a body part in order to generate and/or acquire a plethysmographic waveform. The body part could be a face, forehead, finger, toe or the like. A series of images of the body part captured as video frames may captured by the sensor 126. The series of images may then be processed by either or both of the processors 112, 122. The processing step may involve identifying a region of interest within the series of images, separating each of the series of images, or more specifically each of the regions of interest within the series of images, into one or more channels (e.g. R, G and B), and averaging the pixels within the region of interest. A time-varying signal containing the heart rhythm such as the plethysmographic waveform may be extracted through a series of filtering processes, including, for example, using blind-source separation techniques such as independent component analysis or principal component analysis.

In an illustrative embodiment, the sensor 126 may be a light sensor and may be used in combination with a light source (not shown) to acquire a plethysmographic waveform. The light source, for example a light emitting diode (LED) or laser diode, may be used to illuminate blood-perfused tissue. A light sensor such as a photodiode may be used to measure the absorption of light in the tissue. The intensity of light received by the light sensor varies according to the change in blood volume in the tissue and related light absorption. A plethysmographic waveform may be obtained by using the light sensor to measure the intensity of light that is transmitted through or reflected from the tissue as a function of time. For example, a pulse oximeter may comprise one or more light sources (such as red and infrared wavelengths) and may use one or more light sensors to obtain plethysmographic waveforms.

Autocorrelation Function

At block 204, an autocorrelation function is calculated from the plethysmographic waveform acquired at block 202. Autocorrelation is the correlation of a time series with its own past and future values and a measure of similarity between observations as a function of time lag between them. For example, given a signal x[n], the autocorrelation of x[n] may be defined as:

$$R[\tau] = \sum_n x[n]x[n+\tau]$$

where n is the index and r is the lag at which the autocorrelation function is calculated. In the examples described in the present disclosure, the signal x[n] of the above example may correspond to a plethysmographic waveform.

Figure 3A:
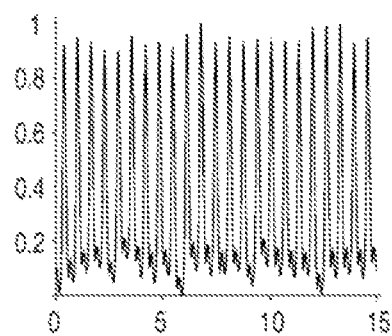
FIGS. 3A-D demonstrate computing the autocorrelation function of plethysmographic waveforms.
Figure 3C:
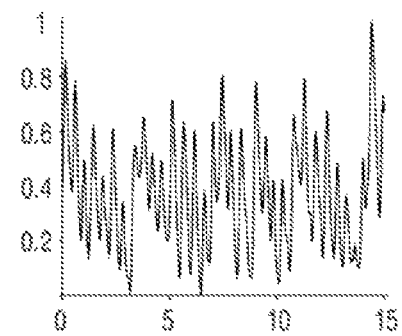
Figure 3B:
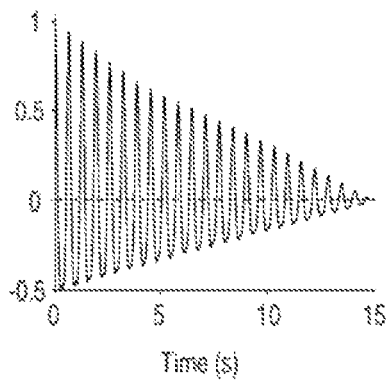

Autocorrelation may uncover repeating patterns in signals, such as semi-periodic signals that may be obscured by noise from motion artifacts etc. FIG. 3B shows the result of performing autocorrelation on a plethysmographic signal (FIG. 3A) in NSR. As can be seen, the resulting autocorrelation function is periodic with high amplitude peaks. The amplitude of the peaks decreases over time. It can also be observed that the autocorrelation function does not exhibit secondary peaks such as the dicrotic notches present in the plethysmogram (FIG. 3A) that can lead to false positives in beat detection.

Figure 3D:
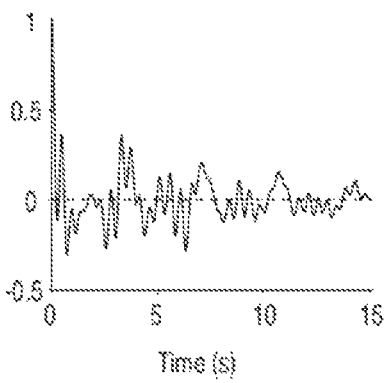

In contrast, a plethysmogram with AF (FIG. 3C) produces an autocorrelation function with markedly different characteristics. When AF is present, the timing between heartbeats changes irregularly. Longer intervals between beats allow for longer filing time, thus the ventricles eject more blood during the next beat. On the other hand, there is less filing time with shorter time intervals so the volume of blood ejected in the following beat is reduced. This is reflected in the non-uniform pattern in the plethysmographic waveform (FIG. 3C). As such, there is little self-similarity and the resulting autocorrelation function is non-periodic with low amplitude peaks (FIG. 3D). Both the amplitude and time interval between peaks in the autocorrelation function appear to vary randomly.

Computing the Features

Figure 4:
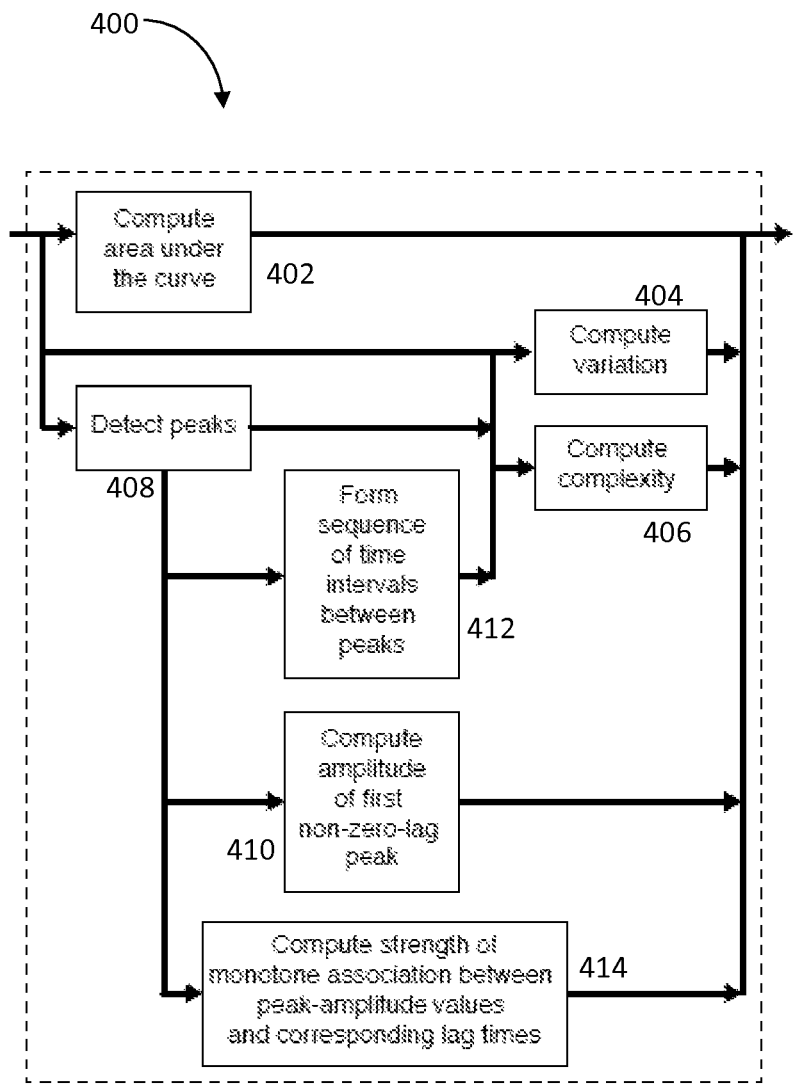
FIG. 4 is a flow chart depicting examples of features that can be computed from the autocorrelation function of the plethysmographic waveform.
Figure 5A:
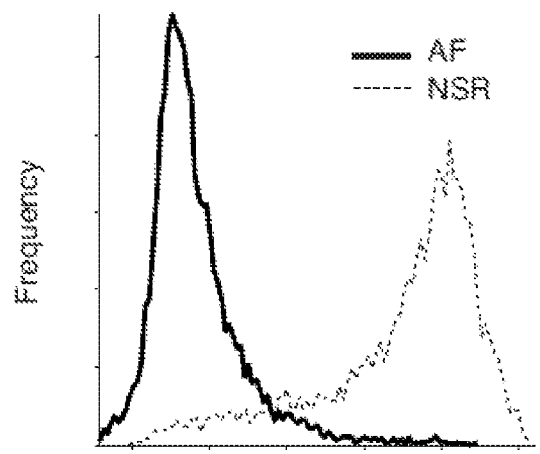
FIGS. 5A-C respectively show distributions of area-under-curve, standard deviation and entropy for NSR and AF autocorrelation functions.

At block 206, one or more features may be computed from the autocorrelation function of the plethysmographic waveform. FIG. 4 is a flow chart 400 depicting examples of features that can be computed from the autocorrelation function of the plethysmographic waveform. For example, at block 402, the area under the autocorrelation curve can be calculated. To avoid negative values, the area-under-curve (AUC) may be computed as the sum of the absolute values of the autocorrelation coefficients. Distributions of AUC values for AF and NSR states are shown in FIG. 5A. The distributions show how this feature is useful for distinguishing AF from NSR because the AUC of autocorrelation functions with AF present are much smaller compared to that of NSR.

Referring back to FIG. 4, an analysis of autocorrelation function coefficient variation may also be performed at block 404. The autocorrelation coefficient for lag τ, $r_\tau$ may be calculated as:

$$r_\tau = \frac{c_\tau}{c_0}$$

where $$c_\tau = \frac{1}{T}\sum_{t=1}^{T-\tau}(y_t - \bar{y})(y_{t+\tau} - \bar{y}),$$

$c_0$ is the sample variance of the time series and T is the length of the time series.

Figure 5B:
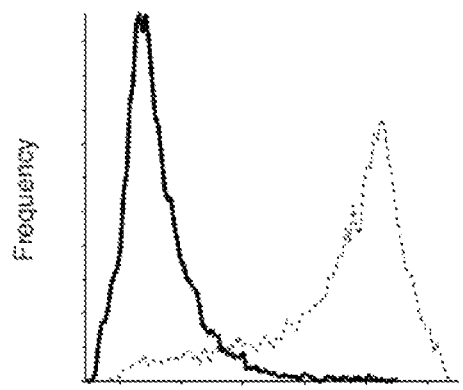

The variation between each autocorrelation coefficient is calculated relative to the mean, the median, consecutive coefficients, or maximum to minimum. For example, the standard deviation of the autocorrelation coefficients is much smaller for AF compared to NSR and may be used for distinguishing between the two states. FIG. 5B shows distributions of standard deviation of autocorrelation coefficients for AF and NSR.

Figure 5C:
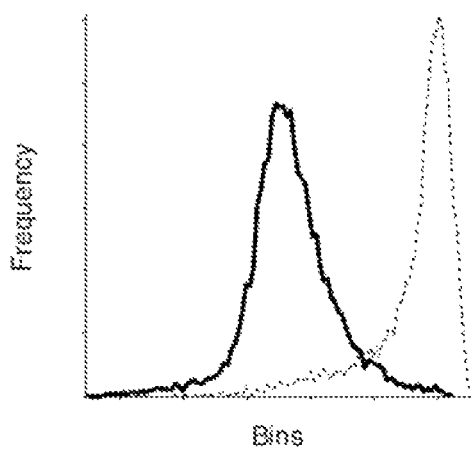

Referring back to FIG. 4, another feature that may be computed from the autocorrelation function is a measure of its complexity at block 406. Complexity measures include measures such as Approximate entropy, Sample entropy, Shannon entropy, Renyi entropy, chaos-based estimates, Komolgorov estimates and the like. For example, FIG. 5C shows distributions of the Sample entropy of the autocorrelation coefficients in an NSR and AF state. When AF is present, the autocorrelation coefficients have lower entropy compared to the NSR state.

Figure 6A:
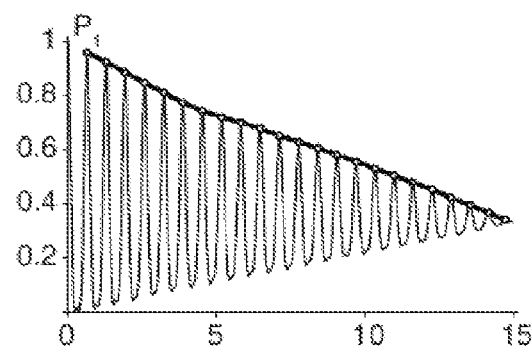
FIGS. 6A-D respectively demonstrate performing peak detection on autocorrelation functions and forming a sequence of time intervals between peaks.
Figure 6C:
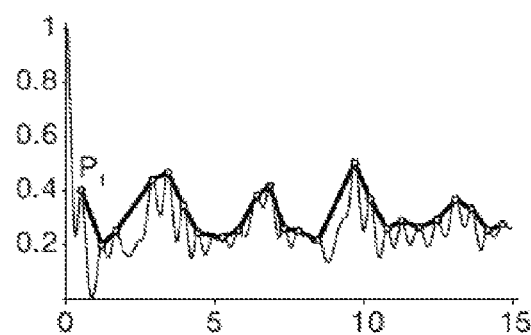
Figure 7A:
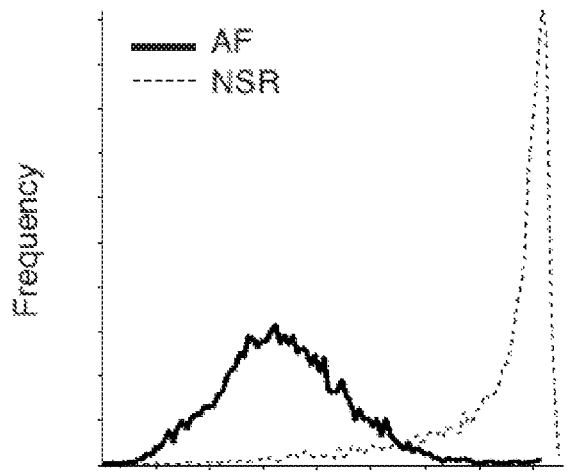
FIGS. 7A-C respectively show distributions of amplitude-of-first-peak, entropy of peak amplitudes, and root-mean-square sequential difference of time intervals between peaks of the autocorrelation functions for NSR and AF.
Figure 7B:
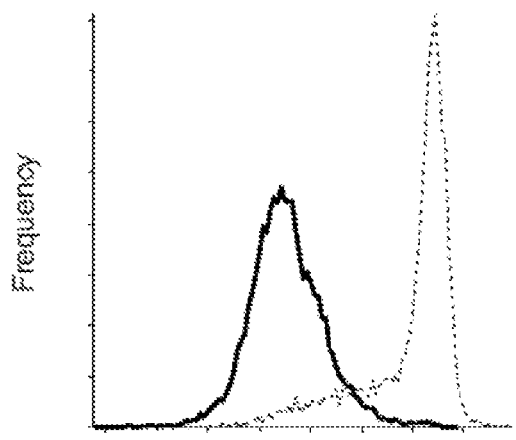

Referring back to FIG. 4, peak detection may be performed on the autocorrelation function for further analysis at block 408. FIGS. 6A and 6C illustrate the peaks detected from the autocorrelation functions in an NSR and AF state respectively. A sequence of peak-amplitude values is produced. The first non-zero-lag peak-amplitude value (P1) may be computed at block 410 and may be used to distinguish AF from NSR as it is much lower when AF is present compared to NSR. FIG. 7A shows distributions of P1 in an NSR and AF state. Analysis of the peak amplitude variation may also be computed at block 404. The variation between each peak-amplitude is calculated relative to the mean, the median, consecutive coefficients, or maximum to minimum. The sequence of peak-amplitudes may also be analyzed in terms of complexity at block 406. For example, FIG. 7B shows distributions of the Sample entropy of the peak-amplitudes in an NSR and AF state. When AF is present, the peak-amplitudes have lower entropy compared to the NSR state. We note that the converse is true when the entropy of the derivative of peak-amplitudes is calculated. Given the randomness of the peak-amplitudes when AF is present, the entropy of the derivative of peak-amplitudes is higher compared to NSR.

Figure 6B:
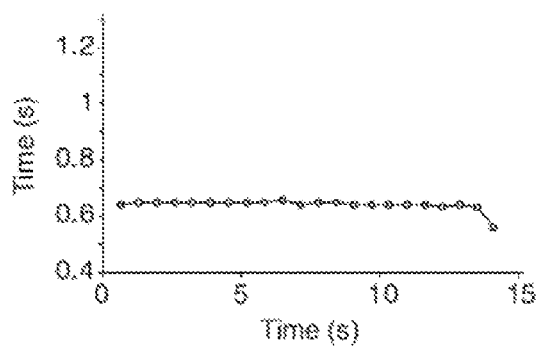
Figure 6D:
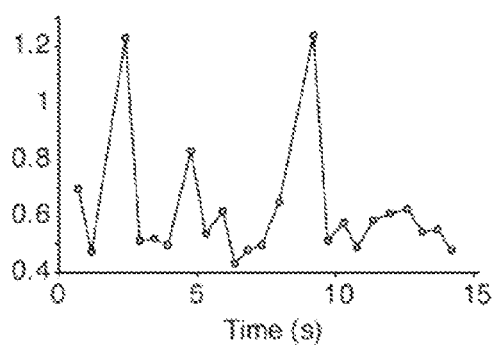
Figure 7C:
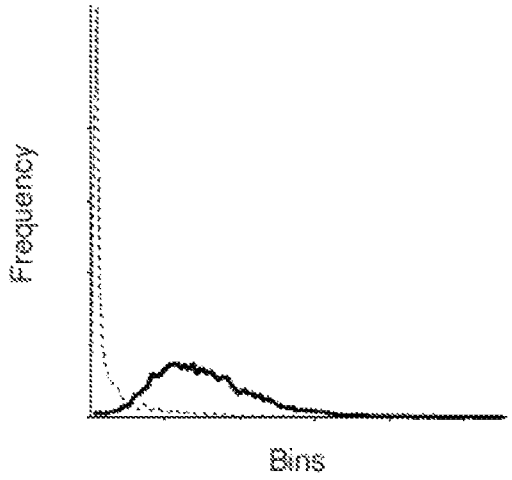

Referring to FIG. 4 and FIGS. 6B and 6D simultaneously, a sequence comprising time-intervals between peaks in the autocorrelation function may be extracted and used for further analysis at block 412. FIGS. 6B and 6D respectively show the resulting sequence of intervals between peaks. It can be observed that in NSR, there is little variation in the time intervals. When AF is present, there is larger variation in the time intervals. At block 404, analysis of the variation between each time interval may be calculated relative to the mean, the median, consecutive coefficients, or maximum to minimum. For example, the root-mean-square sequential difference in time intervals between peaks may be analyzed. This measure captures the irregularity of the heart rhythm and is much higher in AF compared to NSR. FIG. 7C shows distributions of the root-mean-square sequential difference of time intervals between peaks of the autocorrelation functions for NSR and AF. At block 406, the sequence of time intervals between peaks may also be analyzed in terms of complexity using measures such as Approximate entropy, Sample entropy, Shannon entropy, Renyi entropy, chaos-based estimates, Komolgorov estimates and the like.

Referring back to FIG. 4, a sequence of peak-amplitude values and corresponding lag times may be extracted. It can be observed that in NSR, the amplitude of the peaks decreases monotonically (e.g., entirely nonincreasing) over time, as shown in FIG. 6A. When AF is present, the amplitude of the peaks varies randomly and does not exhibit a monotonic decay, as shown in FIG. 6C. At block 414, the strength of a monotone association between peak-amplitude values and lag times may be computed using measures such as Spearman, Kendall, Schweizer-Wolff, monotonicity coefficients, R-estimate and the like. This may also be computed by the percentage of peak-amplitude values that are less than the peak-amplitude value immediately preceding it.

AF Determination

At block 208, one or more of the features described above may be used to perform AF classification. Decision threshold values may be determined for single features. For example, a decision rule may be chosen to minimize the probability of error. When two or more features are combined, a classification function may be performed using standard machine learning algorithms such as discriminant functions, support vector machines, Bayesian networks, decision trees, neural networks and the like. For example, a linear function may be used to compute a score for each possible category (e.g. AF and NSR) by calculating the dot product between a vector comprising the features, and a vector of weights corresponding to each category. The predicted category is the one with the highest score. The procedure for determining the optimal weights may vary depending on the classification function. The classification function may also involve calculating a likelihood of AF based on the feature set.

Figure 8A:
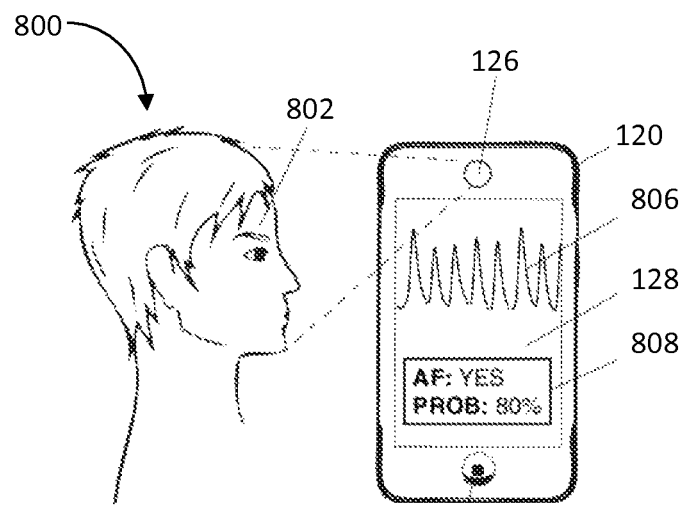
FIGS. 8A and 8B respectively show a human user and a front and rear view of a client device according to aspects of the disclosure.
Figure 8B:
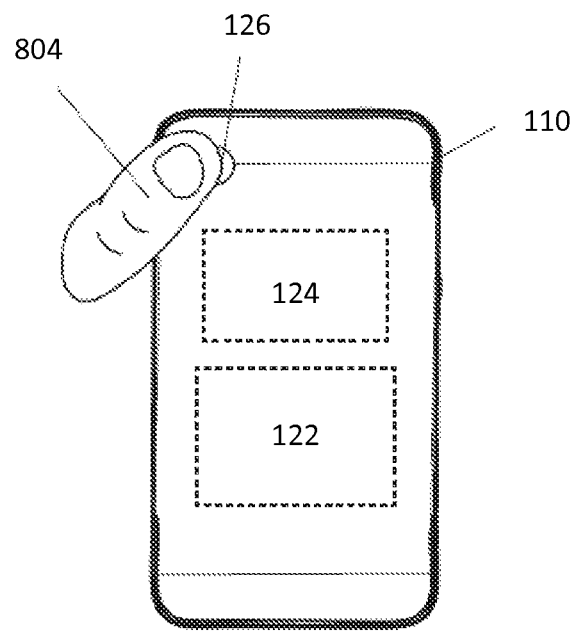

FIGS. 8A and 8B illustrates a human user 800 and a front and rear view of a client device according to aspects of the disclosure. As shown, in FIG. 8A, the sensor 126, e.g., camera, may take a series of images of a user or a portion of a human user, in accordance with the examples set forth above with respect to block 202. In this example, the sensor 126 is capturing images of the face 802 of a user. The processes of blocks 204-208 may then be performed either or both at the client device 120 or at the computer 110. At any time, the plethysmographic waveform 806 may be displayed at the display 128. Additionally, an output 808 may be displayed at the display 128. Such output 808 may include, for example, an AF classification and/or an AF probability. The AF classification may indicate the presence of AF and may be any type of image, text, sound, or any other type of indicia that may be understood by the human user. In the example of FIG. 8A, "YES" may be displayed to indicate the presence of AF.

In other examples, the output 808 may includes a calculated risk score for AF, stroke or other diseases. In this example, the output 808 includes a calculated risk score of 80% to indicate to a user a risk associated with AF. In yet another example, the output 808 may include recommending a course of action based on the classification outcome, such as scheduling an appointment with a doctor/nurse for consultation, adjusting medication levels, changing diet or exercise patterns etc. A user may opt to save the outputs, track changes over time, and also send the analysis results to their care providers.

As shown in FIG. 8B, the sensor 126 may additionally or alternatively acquire a plethysmographic waveform from a finger 804 of the user. Instructions for executing the method of determining presence of AF may be stored at the memory 124 and executed by the processor 122, which may be disposed within the client device 110 as shown in phantom in FIG. 8B. Such instructions may be downloaded from a server in the form of a mobile application that may be available in any type of mobile application marketplace. The instructions may be stored or transmitted to any other type of non-transitory computer readable medium, according to aspects of the disclosure.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, client device 120 may be a television set with a built-in camera, a console gaming system with cameras and/or motion detection capabilities, or a smart watch with a light sensor. Accordingly, this description is meant to be taken only by way of example, and not to otherwise limit the scope of this invention.

What is claimed is:

1. A method for detecting presence of atrial fibrillation, the method comprising:
    acquiring, using one or more sensors, a series of images from a body part;
    extracting a time-varying signal representing a plethysmographic waveform from one or more channels of the series of images;
    calculating an autocorrelation function of the plethysmographic waveform;
    measuring one or more peak amplitudes each corresponding to a height of a peak in the autocorrelation function;
    measuring one or more peak times each corresponding to a location of the peak in the autocorrelation function;
    analyzing, using a processor, the one or more peak amplitudes and the one or more peak times to produce an indication of atrial fibrillation; and
    generating an alert based on the indication of an atrial fibrillation condition.

2. The method according to claim 1, wherein the sensor comprises a camera.

3. The method according to claim 1, wherein the one or more sensors are an element of a at least one of a mobile device or a watch.

4. The method according to claim 1, wherein extracting the time-varying signal representing the plethysmographic waveform further comprises:
    a) identifying a region of interest; and
    b) averaging pixels within the region of interest.

5. The method according to claim 1, wherein the sensor comprises at least one light sensor configured to receive light from a light source.

6. The method according to claim 1, further comprising computing at least one feature from at least one of: area-under-curve, a variation between autocorrelation coefficients, or a complexity of the autocorrelation function.

7. The method according to claim 1, wherein measuring one or more peak amplitudes comprises extracting a sequence of peak-amplitudes from the autocorrelation function using a peak detection algorithm.

8. The method according to claim 7, wherein analyzing the one or more peak amplitudes further comprises computing a strength of a monotone association between peak-amplitudes and corresponding lag times.

9. The method according to claim 1, wherein analyzing the one or more peak amplitudes and the one or more peak times utilizes a machine learning algorithm.

10. The method according to claim 1, wherein generating an alert to the user comprises displaying a result of the AF determination.

11. The method according to claim 10, further comprising displaying an AF probability.

12. The method according to claim 1, wherein measuring one or more peak amplitudes comprises measuring the amplitude of the first non-zero-lag peak in the autocorrelation function.

13. The method according to claim 1, wherein analyzing the one or more peak amplitudes further comprises one or more of: computing variation between the one or more peak amplitudes, and computing complexity between the one or more peak amplitudes.

14. The method according to claim 1, wherein analyzing the one or more peak amplitudes and one or more peak times comprises comparing the one or more peak amplitudes and one or more peak times to respective threshold values.

15. The method according to claim 1, wherein analyzing the one or more peak times further comprises one or more of: computing time intervals between the one or more peak times; computing variation of time intervals between the one or more peak times; or computing complexity of time intervals between the one or more peak times.

16. A system for detecting presence of atrial fibrillation, the system comprising:
    at least one sensor for acquiring a series of images from a body part; and
    a processor configured for extracting a time-varying signal representing a plethysmographic waveform from one or more channels of the series of images, for calculating an autocorrelation function of the plethysmographic waveform, measuring one or more peak amplitudes each corresponding to a height of a peak in the autocorrelation function, measuring one or more peak times each corresponding to a location of a peak in the autocorrelation function, analyzing the one or more peak amplitudes and the one or more peak times to produce an indication of atrial fibrillation, and generating an alert based on the indication of an atrial fibrillation condition.

17. A non-transitory computer-readable storage medium storing a set of instructions capable of being executed by a processor, that when executed by the processor causes the processor to:
    acquire, using one or more sensors, a series of images from a body part;
    extract a time-varying signal representing a plethysmographic waveform from one or more channels of the series of images;
    calculate an autocorrelation function of the plethysmographic waveform;
    measure one or more peak amplitudes each corresponding to a height of a peak in the autocorrelation function;
    measure one or more peak times each corresponding to a location of a peak in the autocorrelation function;
    analyze the one or more peak amplitudes and the one or more peak times to produce an indication of an atrial fibrillation condition;
    and wherein the set of instructions, when executed by the processor, further causes the processor to generate an alert to a user based on the indication of an atrial fibrillation condition.

* * * * *